United States Patent [19]
Witte

[11] 4,165,181
[45] Aug. 21, 1979

[54] OPTICAL ARRANGEMENT IN SPECTROPHOTOMETERS

[75] Inventor: Wolfgang W. F. Witte, Überlingen, Fed. Rep. of Germany

[73] Assignee: Bodenseewerk Perkin-Elmer & Co., GmbH, Überlingen, Fed. Rep. of Germany

[21] Appl. No.: 797,359

[22] Filed: May 16, 1977

[30] Foreign Application Priority Data

May 26, 1976 [DE] Fed. Rep. of Germany ....... 2623653

[51] Int. Cl.² .............................................. G01J 3/42
[52] U.S. Cl. .................................... 356/319; 356/432
[58] Field of Search ........................... 356/39, 88–97, 356/179–186, 188, 189, 201, 204–206, 319–325, 432–436

[56] References Cited

U.S. PATENT DOCUMENTS

| | | | |
|---|---|---|---|
| 2,043,589 | 6/1936 | Müller | 356/179 |
| 3,022,704 | 2/1962 | Cary | 356/324 |
| 3,240,110 | 3/1966 | Öhlin | 356/39 |
| 4,006,900 | 2/1977 | Munk | 356/201 |

*Primary Examiner*—F. L. Evans
*Attorney, Agent, or Firm*—Salvatore A. Giarratana; Francis L. Masselle

[57] ABSTRACT

In a spectrophotometer having a cuvette, a photoelectric detector having a photosensitive surface, a light source arranged for passing a light beam through the cuvette onto the photosensitive surface, an imaging optical system arranged between the cuvette and the photosensitive surface or a rear image thereof being located in a focal plane of the optical system outside the image plane of the light source, whereby the light beam impinges on the photosensitive surface as a relatively large light spot of substantially uniform illumination and, as a result, the location and size of the light spot is not adversely affected by parallel offset, and the demands as to accuracy and alignment of the cuvette are reduced.

3 Claims, 1 Drawing Figure

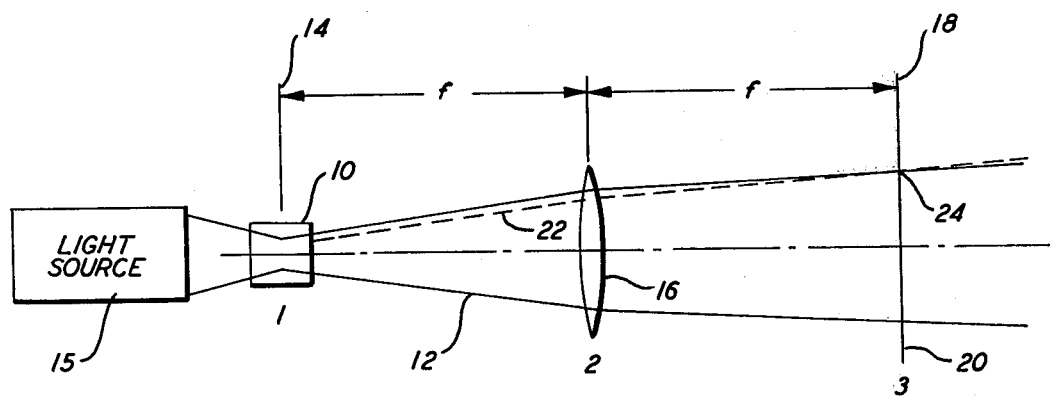

OPTICAL ARRANGEMENT IN SPECTROPHOTOMETERS

BACKGROUND OF THE INVENTION

This invention relates to optical systems for spectrophotometers and, more particularly, to such systems wherein a light beam is passed through a cuvette and then directed onto the photosensitive surface of a photoelectric detector.

It will be appreciated that for accurate measurement, the light beam should always illuminate the same area of the photosensitive surface, because the various areas of this surface, in general, have different sensitivities. Thus, signal variation may result if a light beam is displaced relative to the photosensitive surface. The sample, itself, affects the light beam, as the cuvette filled with the sample is arranged in the path of the light rays. The windows in the cuvette, through which the beam passes, may not be mutually plane parallel, which results in what is known in the art as wedge error. Such a wedge error causes angular deflection of the light beam, but it can be avoided by manufacturing the cuvette in an appropriately precise manner.

In addition, errors result when the individual rays of the light beam are offset, or out of parallel, due to the cuvette with its windows not being mounted normal to the axis of the beam. Parallel offset may also be caused by the beam converging at the location of the cuvette, as the individual rays impinge on the window at an angle which differs from 90°, whereby each ray experiences a corresponding parallel offset. This phenomenon also affects the extent of the area of the photosensitive surface impinged upon by the beam. It will be appreciated that this type of error is particularly aggravating because the parallel offset of the individual converging beams cannot be avoided even by exact alignment of the cuvette and, in addition, it depends on the variable indices of refraction of the samples. It is noted that the indices of refraction of a sample to be tested and of a reference sample, measured earlier or subsequently, may deviate considerably from each other even within the range of the absorption bands of the sample.

It is well known to arrange the cuvette in a collimated portion of the light beam. See, for example, Kortüm, "Kolorimetrie, Photometrie Und Spektrometrie" 4th edition, 1962, page 136, FIG. 69b. In this prior art arrangement, the parallel light beam was subsequently focused on a monochromator entrance slit to form an image of the light source. It required a rather large cross-sectional area of the collimated beam portion at a correspondingly large cross-sectional area of the cuvette to transmit a given light flux, which resulted in an undesirably large sample volume. If the monochromator entrance slit of the prior art arrangement was replaced by a photosensitive surface of a photodetector, an image of the light source would be formed on the photosensitive surface but this surface would not be uniformly illuminated over a large area. Such an arrangement would be extremely sensitive to any kind of angular deflection of the collimated light beam, which would result in displacement of the small, bright light with respect to the photosensitive surface of the detector, and hence move it to an area having a different sensitivity.

SUMMARY OF THE INVENTION

The basic and general object of the present invention is the provision of an optical system for spectrophotometers which overcomes or at least mitigates some of the prior art problems, as outlined hereinbefore.

It is an another object of the invention to provide an optical arrangement in which the light beam impinges upon an extended area of the photosensitive surface, the size and location of this area being substantially unaffected by the sample and the cuvette.

To the accomplishment of the foregoing objectives, and additional objectives and advantages which will become apparent as this description proceeds, the invention contemplates in one form thereof, the provision of a new and improved optical system for a spectrophotometer, which includes a cuvette, a photoelectric detector having a photosensitive surface, a light source arranged for passing a light beam through the cuvette onto the photosensitive surface, and an imaging optical system arranged between the cuvette and the photoelectric detector. According to the invention, the photosensitive surface or a rear image thereof is located in a focal plane of the optical system outside the image plane of the light source.

According to one aspect of the invention, the cuvette is disposed at the location of a constriction of the light beam, and according to another aspect of the invention, the cuvette is disposed in the plane of an image of the light source.

It will be particularly appreciated that, according to the invention, there is no image of the light source formed on the photosensitive surface. Instead, the light beam impinges on the photosensitive surface as a relatively large light spot of substantially uniform illumination. As a result, a parallel offset of the light beam in front of the imaging optical system, due to the sample and cuvette, will not change the location of the point on which the light ray impinges upon the photosensitive surface, and consequently, the location and size of the light spot formed on the photosensitive surface is not adversely affected by parallel offset, and the demands as to accuracy and alignment of the cuvette are reduced. In particular, it is possible, without disadvantageous errors, to arrange the cuvette in a conversion path of rays, and thus in a constriction of the beam, so that the total light flux of the beam can be concentrated on a relatively small cuvette.

There has thus been outlined rather broadly the more important features of the invention in order that the detailed description thereof that follows may be better understood, and in order that the present contribution to the art may be better appreciated. There are, of course, additional features of the invention which will be described more fully hereinafter. Those skilled in the art will appreciate that the conception on which this disclosure is based may readily be utilized as the basis of designing of other structures for carrying out the various purposes of the invention. It is important, therefore, that this disclosure be regarded as including such equivalent constructions as do not depart from the spirit and scope of the invention.

One embodiment of the invention has been chosen for purposes of illustration and description and is shown in the accompanying drawing forming a part of the specification.

BRIEF DESCRIPTION OF THE DRAWING

The FIGURE is a schematic illustration of pertinent elements of a spectrophotometer, illustrating schematically the path of the light rays in an optical system according to the present invention.

DETAILED DESCRIPTION OF THE PREFERRED EMBODIMENTS

In the embodiment of the invention illustrated in the drawing, a spectrophotometer includes a cuvette 10 for containing a sample to be tested. The cuvette 10 is located in the converging path of the rays of a beam 12, in the plane 14 of an image of a light source, indicated at 15. That is, the cuvette 10 is located in a constriction of the light beam 12. Behind or subsequent to the cuvette 10, the light beam 12 again diverges, as is clearly seen in the drawing. From the cuvette, the light beam 12 passes through an imaging optical system illustrated in the form of a lens 16 having a focal length f. A photosensitive surface 20 of a photoelectric detector is located in the rear focal plane 18 of the lens 16, and the light beam 12 impinges on this photosensitive surface in the form of a relatively extended, substantially uniformly illuminated light spot. It will be particularly appreciated that the photosensitive surface 20 is located outside the image plane of the light source.

A feature of the present invention resides in the fact that if a parallel offset of a light ray is caused by the sample, as indicated by the ray 22 shown as a broken line, this parallel offset will not change the point 24 of penetration of the light ray through the focal plane 18, and thus will not change the location thereof on the photosensitive surface 20. That is, the light spot illuminated on the surface 20 is independent, as to location and size, of such parallel offset, whereby the light beam always impinges on the same areas of the photosensitive surface 20 to thereby provide a photoelectric detector of constant sensitivity.

In addition, the arrangement according to the invention is substantially independent of angular deflection, caused by the cuvette due, for example, to wedge error. Actually, such deflection causes a small displacement of the light spot with respect to the photosensitive surface 20, but in view of the fact that the dimensions of the substantially uniform illuminated light spot are large as compared to this displacement, the displacement has only a slight influence on the total signal of the photoelectric detector.

Having thus described the invention with particular reference to the preferred form thereof, it will be obvious to those skilled in the art to which the invention pertains, after understanding the invention, that various changes and modifications may be made therein without departing from the spirit and scope of the invention, as defined by the claims appended hereto.

What is claimed is:

1. A spectrophotometer comprising,
   a cuvette,
   a photoelectric detector having a photosensitive surface,
   a light source arranged for passing a light beam through said cuvette onto said photosensitive surface,
   an imaging optical system arranged between said cuvette and said photoelectric detector, said imaging optical system having a front principal focal plane and a rear principal focal plane having substantially equal focal lengths, said cuvette being located in the front focal plane and said photosensitive surface being located in the rear principal focal plane which is outside the image plane of said light source, so that deflection of a beam of light in the cuvette will not substantially change the location thereof on the photosensitive surface.

2. A spectrophotometer according to claim 1 wherein said cuvette is arranged at the location of a constriction of the light beam.

3. A spectrophotometer according to claim 1 wherein said cuvette is disposed in the plane of an image of the light source.

* * * * *